(12) United States Patent
Hebrank

(10) Patent No.: US 6,850,316 B2
(45) Date of Patent: Feb. 1, 2005

(54) METHODS AND APPARATUS FOR HARVESTING VACCINE FROM EGGS

(75) Inventor: John H. Hebrank, Durham, NC (US)

(73) Assignee: Embrex, Inc., Durham, NC (US)

( * ) Notice: Subject to any disclaimer, the term of this patent is extended or adjusted under 35 U.S.C. 154(b) by 189 days.

(21) Appl. No.: 10/166,919

(22) Filed: Jun. 10, 2002

(65) Prior Publication Data

US 2003/0227613 A1 Dec. 11, 2003

(51) Int. Cl.[7] .............................. A01K 4/00; A01K 4/04
(52) U.S. Cl. .............................. 356/53; 356/54; 356/58; 209/511
(58) Field of Search .............................. 356/53, 54, 58; 209/510, 511

(56) References Cited

U.S. PATENT DOCUMENTS

| | | | |
|---|---|---|---|
| 3,616,262 A | 10/1971 | Coady | 195/127 |
| 4,671,652 A | 6/1987 | van Aselt et al. | 356/66 |
| 4,681,063 A | 7/1987 | Hebrank | 119/1 |
| 4,914,672 A | 4/1990 | Hebrank | 374/124 |
| 4,955,728 A | 9/1990 | Hebrank | 374/124 |
| 5,017,003 A | 5/1991 | Keromnes et al. | 356/53 |
| 5,173,737 A | 12/1992 | Mitchell et al. | 356/53 |
| 5,745,228 A | 4/1998 | Hebrank et al. | 356/53 |
| 5,900,929 A | 5/1999 | Hebrank et al. | 356/52 |
| 6,145,668 A | 11/2000 | DePauw et al. | 209/510 |
| 6,149,375 A | 11/2000 | Hebrank | 414/737 |
| 6,213,709 B1 | 4/2001 | Hebrank | 414/737 |
| 6,224,316 B1 | 5/2001 | Hebrank et al. | 414/404 |

OTHER PUBLICATIONS

Copy of International Search Report for PCT/US03/01912.

Primary Examiner—Zandra V. Smith
(74) Attorney, Agent, or Firm—Myers Bigel Sibley & Sajovec, P.A.

(57) ABSTRACT

Methods and apparatus for producing vaccine within a plurality of eggs are provided. Each of a plurality of eggs is illuminated with light from one or more LEDs. A detector is positioned adjacent each egg and detects light passing therethrough. Each egg is then identified as containing a live embryo or as being a non-live egg. Each egg that is determined not to contain a live embryo may be removed, either automatically or by hand. A seed virus is injected into each egg identified as containing a live embryo. After a predetermined period of incubation each live embryo is euthanized and amniotic fluid containing a vaccine produced as a result of the presence of a seed virus is harvested from each euthanized egg.

13 Claims, 11 Drawing Sheets

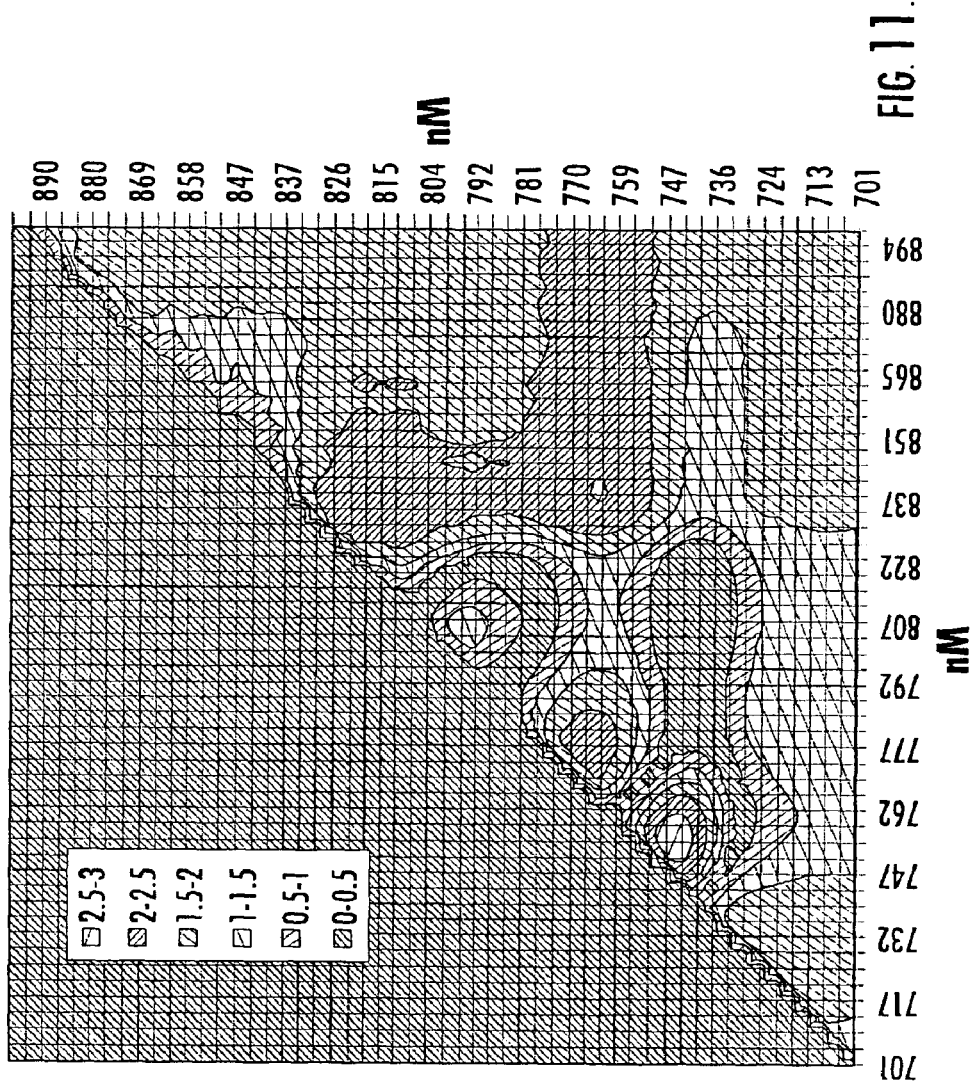

METHODS AND APPARATUS FOR HARVESTING VACCINE FROM EGGS

FIELD OF THE INVENTION

The present invention relates generally to eggs and, more particularly, to methods and apparatus for processing eggs.

BACKGROUND OF THE INVENTION

Discrimination between poultry eggs on the basis of some observable quality is a well-known and long-used practice in the poultry industry. "Candling" is a common name for one such technique, a term which has its roots in the original practice of inspecting an egg using the light from a candle. As is known to those familiar with eggs, although egg shells appear opaque under most lighting conditions, they are in reality somewhat translucent, and when placed in front of a direct light, the contents of the egg can be observed.

An egg may be a "live" egg, meaning that it has a viable embryo. FIG. 1A illustrates a live poultry egg 1 at about day one of incubation. FIG. 1B illustrates the live egg 1 at about day eleven of incubation. The egg 1 has a somewhat narrow end in the vicinity represented at 1a as well as an oppositely disposed broadened end portion in the vicinity shown at 1b. In FIG. 1A, an embryo 2 is represented atop the yolk 3. The egg 1 contains an air cell 4 adjacent the broadened end 1b. As illustrated in FIG. 1B, the wings 5, legs 6, and beak 7 of a baby chick have developed.

An egg may be a "clear" or "infertile" egg, meaning that it does not have an embryo. More particularly, a "clear" egg is an infertile egg that has not rotted. An egg may be an "early dead" egg, meaning that it has an embryo which died at about one to five days old. An egg may be a "mid-dead" egg, meaning that it has an embryo which died at about five to fifteen days old. An egg may be a "late-dead" egg, meaning that it has an embryo which died at about fifteen to eighteen days old.

An egg may be a "rotted" egg, meaning that the egg includes a rotted infertile yolk (for example, as a result of a crack in the egg's shell) or, alternatively, a rotted, dead embryo. While an "early dead", "mid-dead" or "late-dead egg" may be a rotted egg, those terms as used herein refer to such eggs which have not rotted. Clear, early-dead, mid-dead, late-dead, and rotted eggs may also be categorized as "non-live" eggs because they do not include a living embryo.

Eggs which are to be hatched to live poultry are typically candled during embryonic development or later to identify clear, rotted, and dead eggs (collectively referred to herein as "non-live eggs") and remove them from incubation to thereby increase available incubator space. U.S. Pat. Nos. 4,955,728 and 4,914,672, both to Hebrank, describe a candling apparatus that uses infrared detectors and the infrared radiation emitted from an egg to distinguish live from infertile eggs.

U.S. Pat. No. 4,671,652 to van Asselt et al. describes a candling apparatus in which a plurality of light sources and corresponding light detectors are mounted in an array, and wherein eggs are passed on a flat between the light sources and the light detectors.

Other applications where it is important to be able to distinguish between live and non-live eggs are becoming important. One of these applications is cultivation and harvesting of human flu vaccines via live eggs. Human flu vaccine production is accomplished by injecting seed virus into a chicken egg at about day eleven of embryonic development (day-11 egg), allowing the virus to grow for about two days, euthanizing the embryo by cooling the egg, and then harvesting the amniotic fluid from the egg.

Typically, eggs are candled before injection of a seed virus to remove non-live eggs. The fluid surrounding virtually all early and mid-dead eggs in many hatcheries tend to have a white, milky appearance and are referred to in the industry as "milky" eggs. It is surmised that the procedure of washing an egg prior to incubation may produce a milky egg either by the wash solution transporting pathogens into the egg or because the washing removes some of the protective cuticle on the egg shell. Unfortunately, the embryo of a Day-11 egg may block as much light from a candling apparatus as a milky egg. As a result, it may be difficult to distinguish between milky early dead eggs and live eggs at this stage of embryonic development.

SUMMARY OF THE INVENTION

In view of the above discussion, embodiments of the present invention provide methods and apparatus for identifying whether an egg, particularly an egg at day eleven of incubation (day-11 egg), contains a live embryo. An egg is illuminated with light from a light emitting diode (LED) at wavelengths of between about 650 nm–850 nm. Light passing through the egg is received at a detector positioned adjacent the egg, and the egg is then identified as containing a live embryo if detected light is less than a preset value, or the egg is identified as a non-live egg if detected light is greater than the preset value.

According to embodiments of the present invention, illuminating an egg may include directing one or more pulses of light at an egg at wavelengths of between about 650 nm–850 nm. According to embodiments of the present invention, illuminating an egg may include directing a pulse of light having a peak wavelength of about 700 nm and a half-power spectral width of less than about 100 nm at the egg.

According to embodiments of the present invention, identifying whether an egg contains a live embryo may include illuminating the egg with light from a first LED at wavelengths selected from the wavelength bands consisting of 830 nm–1000 nm, 710 nm–800 nm, 880 nm–900 nm, and with light from a second LED at wavelengths selected from the wavelength bands consisting of 700 nm–830 nm, 700 nm–775 nm, 830 nm–880 nm. Light passing through the egg is received by a detector positioned adjacent the egg, and the egg is identified as containing a live embryo if detected light from the first LED is less than a first preset value and if the value of the detected light from the first LED divided by the value of the detected light from the second LED is less than a second preset value. Alternatively, the egg may be identified as a non-live egg if detected light from the first LED is greater than the first preset value and if detected light from the second LED divided by the detected light from the first LED is greater than the second preset value.

According to embodiments of the present invention, methods of producing vaccine within a plurality of eggs are provided. Each of a plurality of eggs is illuminated with light from one or more LEDs. A detector is positioned adjacent each egg and detects light passing therethrough. Each egg is then identified as containing a live embryo or as being a non-live egg. Each egg that is determined not to contain a live embryo (e.g., dead, clear, etc.) may be removed, either automatically or by hand. A seed virus (or multiple seed viruses) is injected in ovo into each egg identified as containing a live embryo.

After a predetermined period of incubation (e.g., between 2–5 days) each live embryo is euthanized and amniotic fluid (or other material) containing a vaccine produced as a result of the presence of a seed virus is harvested from each euthanized egg.

BRIEF DESCRIPTION OF THE DRAWINGS

FIGS. 10–11 are plots that illustrate the discrimination ratio for two groups of selected eggs using a number equal to the ratio of light values at two different wavelengths.

DETAILED DESCRIPTION OF THE INVENTION

The present invention now is described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Methods and apparatus according to embodiments of the present invention may be utilized for identifying whether an egg contains a dead or live embryo at any time during the embryonic development period (also referred to as the incubation period) of the egg. Embodiments of the present invention are not limited to identification at a particular day (e.g., day eleven) during the embryonic development period. In addition, methods and apparatus according to embodiments of the present invention may be used with any types of avian eggs, including chicken, turkey, duck, geese, quail, and pheasant eggs.

Figure 1B:
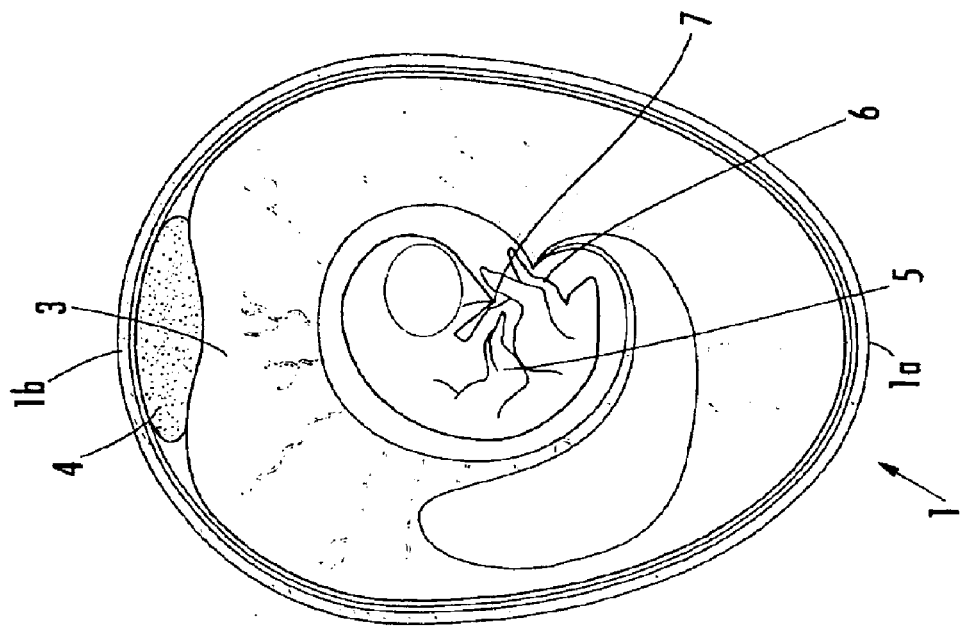
FIG. 1B illustrates a live chicken egg at about day eleven of incubation.
Figure 1A:
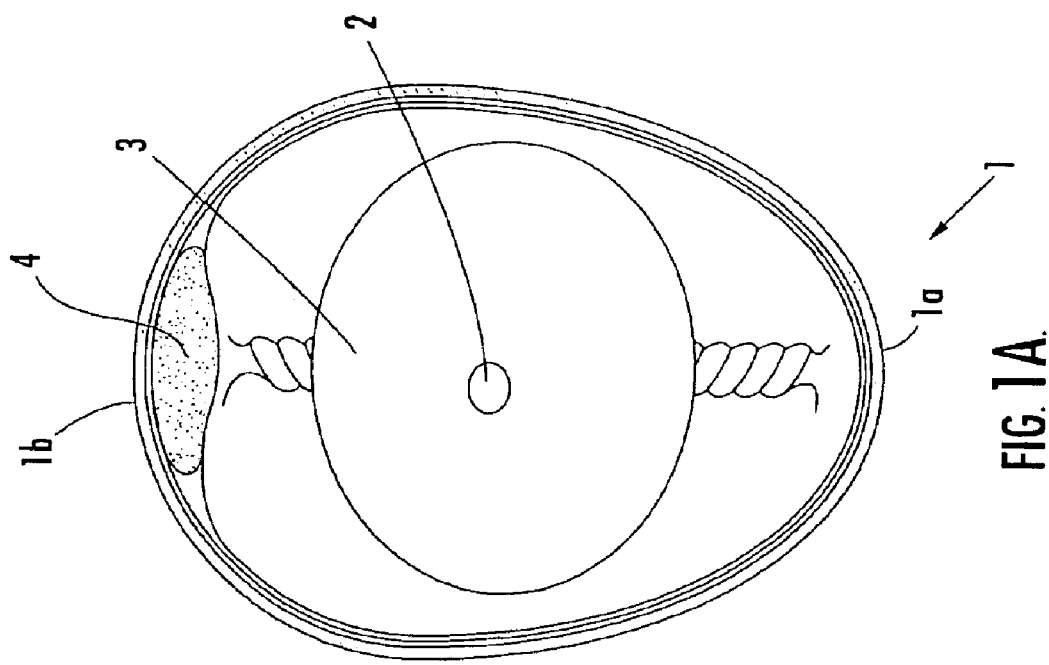
FIG. 1A illustrates a live chicken egg at about day one of incubation.
Figure 2:
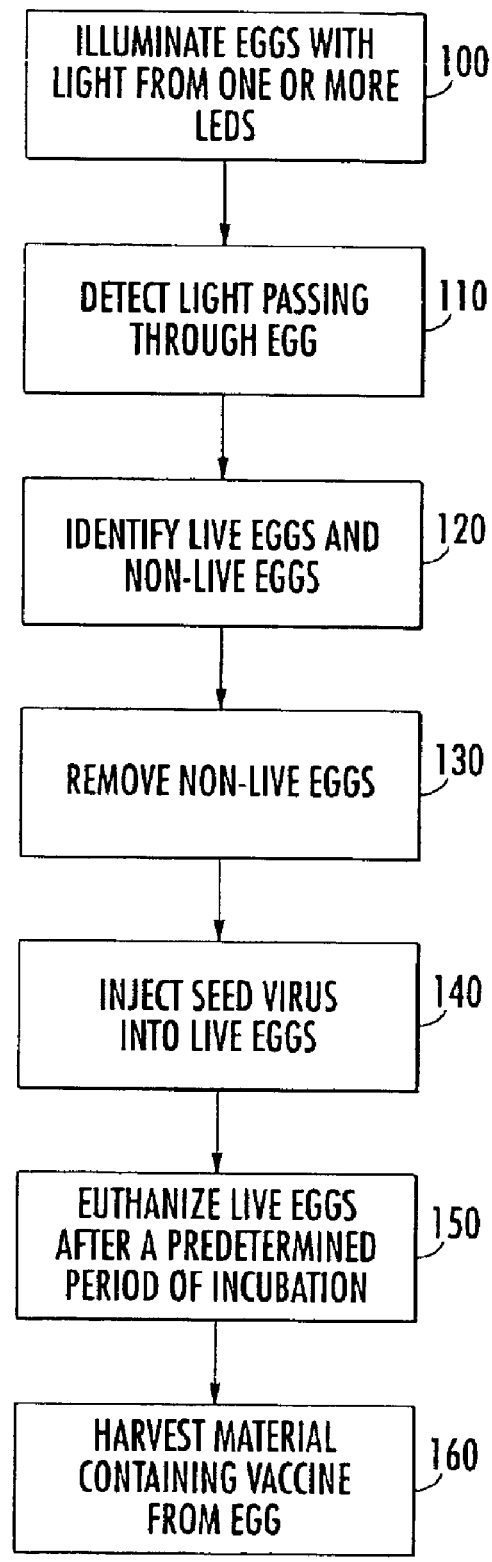
FIG. 2 is a flowchart of operations for producing vaccines within a plurality of eggs, according to embodiments of the present invention.

Referring now to FIG. 2, a method of producing vaccine within a plurality of eggs, according to embodiments of the present invention, is illustrated. Each of a plurality of day-11 eggs is illuminated with light from one or more light sources at wavelengths of between about six hundred fifty nanometers and about eight hundred fifty nanometers (650 nm–850 nm) (Block 100). Preferred light sources include light emitting diodes (LEDs).

As is known to those skilled in the art, an LED is a semiconductor device that emits light when an electric current is passed therethrough. The output from an LED can range from red (at a peak wavelength of about 695 nanometers) to blue-violet (at a peak wavelength of about 400 nanometers). LEDs that emit infrared (IR) energy (830 nanometers or longer) may also be utilized in accordance with embodiments of the present invention.

Each light source is positioned adjacent an egg (e.g., at or near the pointed or non-air cell end of an egg). Each light source may be in contacting relationship with an egg, and/or a light beam from the light source may be collimated into a narrow beam (typically less than ±10 degrees), such that less light will be scattered off adjacent eggs and into the detector of an egg.

According to embodiments of the present invention, illuminating each day-11 egg with light from one or more light sources may include directing one or more pulses of light at each egg at wavelengths of between about six hundred fifty nanometers and about eight hundred fifty nanometers (650 nm–850 nm). According to other embodiments of the present invention, illuminating an egg with light from one or more light sources may include directing a pulse of light having a peak wavelength of about 695 nanometers and a half-power spectral width of less than about 100 nanometers at each egg.

According to embodiments of the present invention, dual light sources may be utilized to direct one or more pulses of light at each egg in the following wavelength bands:

| Wavelength A | Wavelength B |
|---|---|
| 830–1000 nm | 700–830 nm |
| 710–800 nm | 700–775 nm |
| 880–900 nm | 830–880 nm |

A detector is positioned adjacent each egg and detects light passing therethrough (Block 110). Each egg is then identified as containing a live embryo or as being a non-live egg (Block 120). According to embodiments of the present invention, an egg contains a live embryo if detected light is less than a preset value and an egg is a non-live egg if detected light is greater than the preset value. A preset value may be a particular intensity of light. For example, a preset value may be a certain level (e.g., 0.1 microwatt per square centimeter) and/or may be a certain percentage of transmitted light within one or more frequency bands, or the ratio of the transmitted light at two different wavelengths.

According to embodiments of the present invention, a light source and detector may be positioned on respective opposite portions of a respective egg. For example, each respective light source and detector may be positioned on respective opposite end portions of an egg. However, a light source and a detector need not be positioned directly opposite from one another. A light source and detector may be positioned adjacent an egg in any of various configurations and orientations, without limitation.

Each egg that is determined not to contain a live embryo (e.g., dead, clear, cracked, rotted, etc.) may be removed, either automatically or by hand (Block 130). Removed eggs may be discarded or may be subjected to additional processing for various purposes. A seed virus (or multiple seed viruses) is injected into each egg identified as containing a live embryo (Block 140). For example, a human flu virus may be injected into each egg identified as containing a live embryo.

An exemplary device for injecting a seed virus into a plurality of eggs in accordance with embodiments of the present invention is the INOVOJECT® automated injection system (Embrex, Inc., Research Triangle Park, N.C.). However, any in ovo injection device may be suitable for use according to embodiments of the present invention. Suitable injection devices preferably are designed to operate in conjunction with commercial egg carrier devices or flats.

After a predetermined period of incubation (e.g., between 2–5 days) each live embryo is euthanized (Block 150) and amniotic fluid (or other material) containing a vaccine produced as a result of the presence of a seed virus is harvested from each euthanized egg (Block 160). For example, if a seed virus injected into an egg is a human flu virus, the harvested amniotic fluid (or other material) contains human flu vaccine.

Figure 3:
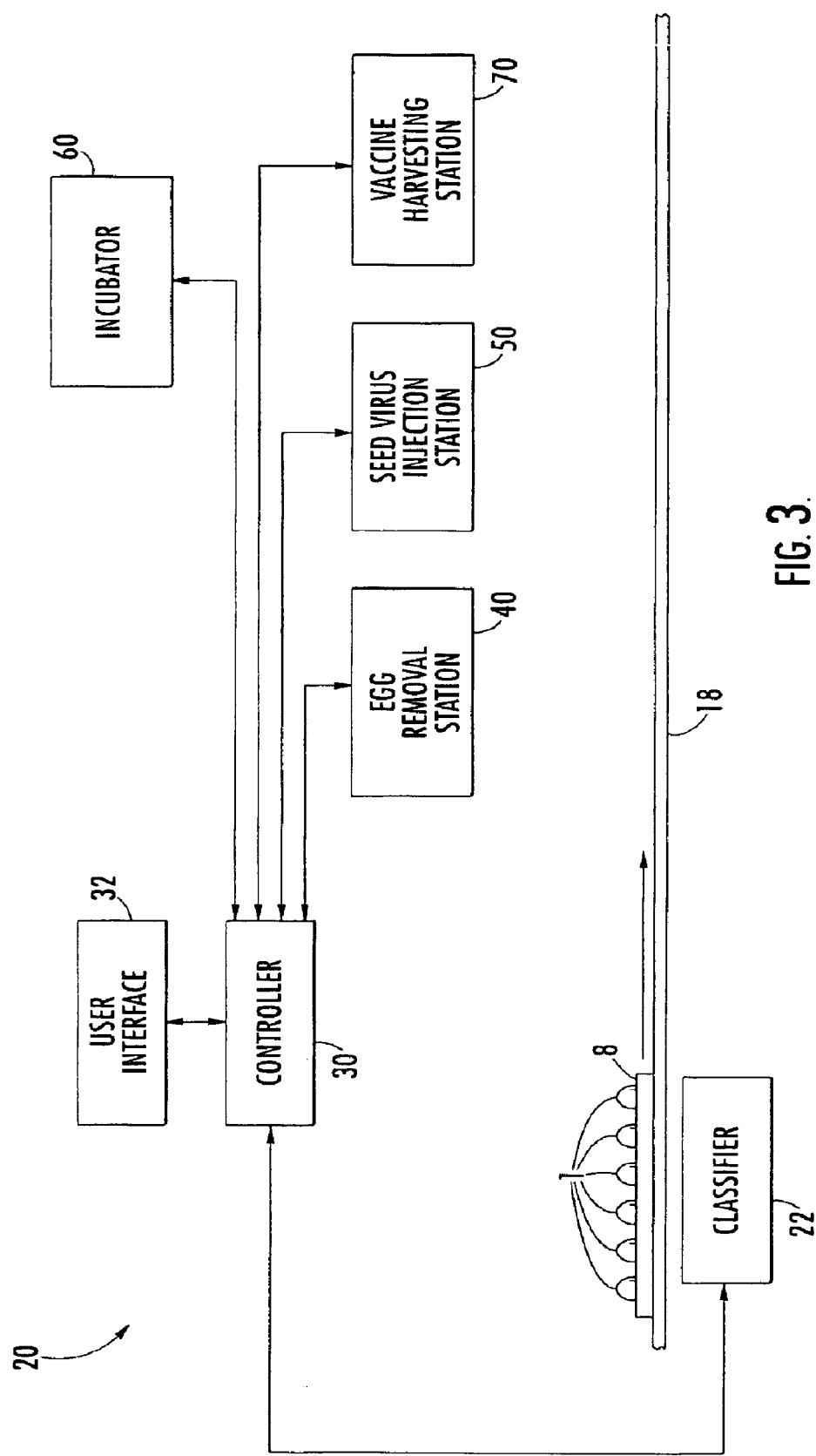
FIG. 3 is a block diagram of a system for producing vaccines within a plurality of eggs, according to embodiments of the present invention.

Referring now to FIG. 3, an apparatus 20 for producing vaccine within a plurality of eggs according to embodiments of the present invention is illustrated. The illustrated apparatus 20 includes a classifier 22 that is configured to identify eggs containing live embryos and to identify non-live eggs from among a plurality of eggs 1 in an incoming egg flat 8. The classifier 22 is operatively connected to a controller 30 which controls the classifier 22 and stores information about each egg 1 (e.g., whether an egg contains a live embryo or not, etc.). The classifier 22 includes a plurality of light sources (LEDs) and detectors operably associated with a respective egg 1 in the flat 8. An operator interface (e.g., a display) 32 is preferably provided to allow an operator to interact with the controller 30.

Figure 4:
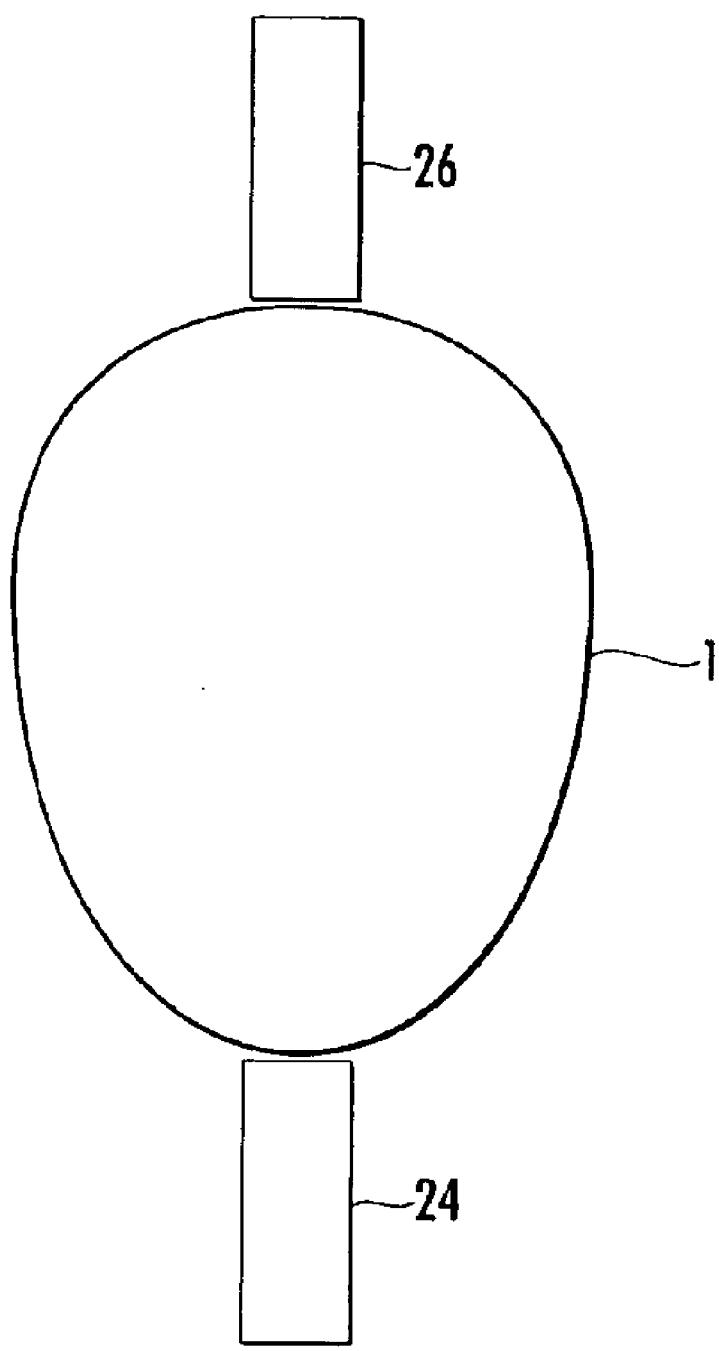
FIG. 4 is a block diagram of a light source and detector for identifying whether an egg in day eleven of incubation (day-11 egg) contains a live embryo, according to embodiments of the present invention.

FIG. 4 illustrates an exemplary light source (e.g., an LED) 24 and light detector 26 positioned adjacent opposite portions of an egg 1. According to a preferred embodiment, an illumination beam is generated by a 700 nM LED (ELD-700-524-3 from Roithner Lasertechnik, Vienna Austria) having a ±10 degree beam angle located approximately 2 cm above an egg. The LED is placed in a cavity approximately 2 cm deep and 2 cm in diameter with a 0.8 cm diameter aperture. The cavity and aperture function as described in U.S. Pat. Nos. 5,900,929 and 5,745,228, which are assigned to the assignee of the present invention, and which are incorporated herein by reference in their entireties, to reduce stray light that is emitted outside of the central beam.

A preferred detector is an IPL 10530DAL, from Integrated Photomatrix Limited, Dorchester Dorset, UK and is mounted about 2 cm from an egg and directly below it. According to an embodiment of the present invention, there is one emitter-detector pair for each position in a row of eggs so that as a flat of eggs passes under the unit all eggs on the flat will be scanned by the array. Emitters are pulsed on for about 70 microseconds, one at a time, to eliminate light from one egg reflecting into an adjacent detector. The output of each detector is recorded immediately before its LED is pulsed on, during the on time, and afterwards. The recorded reading is the detector output while the LED is on minus the average of the light levels before and after that period. The scanning pattern allows each egg in a row to be sampled about 200 times per second.

Embodiments of the present invention do not require that a respective light source (or sources) and detector be provided for each egg in a flat. Various numbers and combinations of light sources and detectors may be utilized without limitation.

An egg removal station 40, seed virus injection station 50, and vaccine harvesting station 70 are provided downstream of the classifier 22 and are each operatively connected to the controller 30. The seed virus injection station 50 is configured to inject one or more seed viruses into each egg 1 within a flat 8 that is identified as containing a live embryo.

Figure 5:
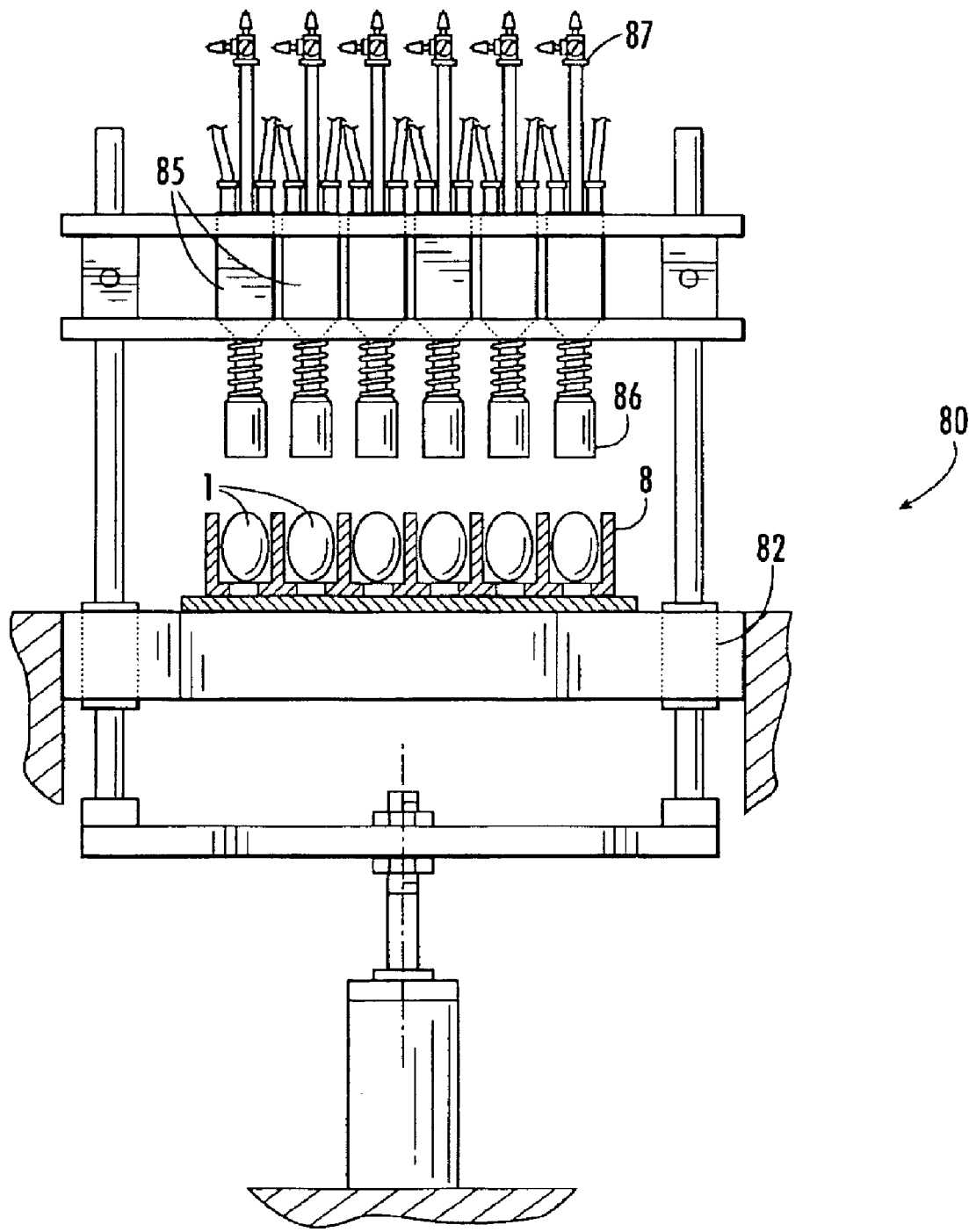
FIG. 5 is a side view of a multiple injection head in ovo injection/material removal device with which virus delivery devices and methods, as well as material removal devices and methods, according to embodiments of the present invention may be used.

FIG. 5 illustrates an exemplary apparatus 80 that may be utilized to inject a seed virus into a plurality of eggs in ovo, as well as to remove material from a plurality of eggs, according to embodiments of the present invention. The illustrated apparatus 80 includes a flat 8 for carrying eggs 1, a stationary base 82, and a plurality of injection delivery devices, or heads, 85 with fluid delivery means such as lumens or needle(s) positioned therein in accordance with known techniques. The flat 8 holds a plurality of eggs 1 in a substantially upright position. The flat 8 is configured to provide external access to predetermined areas of the eggs 1. Each egg 1 is held by the flat 8 so that a respective end thereof is in proper alignment relative to a corresponding one of the injection heads 85 as the injection head 85 advances towards the base 82 of the apparatus. However, in ovo injection (and in ovo material removal) devices may inject (or remove material from) eggs in various orientations. Embodiments of the present invention are not limited only to in ovo injection and/or removal devices that inject (or remove material from) eggs in the illustrated orientation.

Each of the plurality of injection heads 85 has opposing first and second ends 86, 87. The heads 85 have a first extended position and a second retracted position, as is known in the art. Upon extension of an injection head 85, the first end 86 is configured to contact and rest against predetermined areas of an external egg shell. When not injecting (or removing material from an egg), the injection heads 85 are retracted to rest a predetermined distance above the eggs 1 and stationary base 82. Alternatively, the base 82 can be longitudinally slidably moveable to position the eggs 1 in proper position relative to the injection heads 85.

Referring back to FIG. 3, the egg removal station 40 is configured to remove eggs identified as non-live. The controller 30 generates a selective removal signal for an egg 1 based upon whether the classifier 22 identified the egg 1 as being non-live. The egg removal station 40 may employ suction-type lifting devices as disclosed in U.S. Pat. No. 4,681,063 or in U.S. Pat. No. 5,017,003 to Keromnes et al., the disclosures of which are hereby incorporated by reference in their entireties. Various devices and methods for removing eggs may be utilized with embodiments of the present invention without limitation. Exemplary egg removal apparatus that may serve the function of the egg removal station 40 are described in U.S. Pat. Nos. 6,145,668; 6,149,375; 6,213,709; and 6,224,316, each of which is incorporated herein by reference in its entirety.

The egg removal station 40 preferably operates automatically and robotically. Alternatively, selected eggs may be identified on the user interface 32, optionally marked, and removed by hand.

After injection with a seed virus, the eggs 1 containing live embryos are transferred to an incubator 60 for a predetermined period of time. At the end of this period of time, the eggs 1 are transferred to the vaccine harvesting station 70 where material from each egg 1 (e.g., amniotic fluid) is extracted. An exemplary device that may be adapted for use as a vaccine harvesting device in accordance with embodiments of the present invention is the INOVOJECT® automated injection system.

The controller 30 preferably includes a processor or other suitable programmable or non-programmable circuitry including suitable software. The controller 30 may also include such other devices as appropriate to control the classifier 22, the egg removal station 40, the seed virus injection station 50, the incubator 60, and the vaccine harvesting station 70. Suitable devices, circuitry and software for implementing a controller 30 will be readily apparent to those skilled in the art upon reading the description herein and the disclosures of U.S. Pat. No. 5,745,228 to Hebrank et al. and U.S. Pat. No. 4,955,728 to Hebrank, which are incorporated herein by reference in their entireties.

The operator interface 32 may be any suitable user interface device and may include a touch screen and/or keyboard. The operator interface 32 may allow a user to retrieve various information from the controller 30, to set various parameters and/or to program/reprogram the controller 30. The operator interface 32 may include other peripheral devices, for example, a printer and a connection to a computer network.

According to alternative embodiments of the present invention, one or more of the stations (40,50,60,70) described with respect to FIG. 3 may be controlled by individual programmable logic controllers (PLCs). Data may be transferred back and forth from a PLC to a central computer database controller for storage. For example, a central database may be provided to store information about eggs being processed. The central computer database controller may be configured to respond to individual PLCs when they request data or send data. The central computer database need not directly control the various stations under the control of respective PLCs.

A conveying system 18 serves to transport a flat 8 of eggs 1 through and, optionally, between, the classifier 22, the egg removal station 40, the seed virus injection station 50, the incubator 60, and the vaccine harvesting station 70. Egg conveying systems are well known to those of skill in the art and need not be described further herein.

Although eggs conventionally are carried in egg flats, any means of presenting a plurality of eggs over time to the classifier 22, the egg removal station 40, the seed virus injection station 50, the incubator 60, and the vaccine harvesting station 70 can be used.

Egg flats of virtually any type may be used in accordance with embodiments of the present invention. Flats may contain any number of rows, such as seven rows of eggs, with rows of six and seven being most common. Moreover, eggs in adjacent rows may be parallel to one another, as in a "rectangular" flat, or may be in a staggered relationship, as in an "offset" flat. Examples of suitable commercial flats include, but are not limited to, the "CHICKMASTER 54" flat, the "JAMESWAY 42" flat and the "JAMESWAY 84" flat (in each case, the number indicates the number of eggs carried by the flat). Egg flats are well known to those of skill in the art and need not be described further herein.

Embodiments of the present invention are not limited just to eggs located in flats prior to vaccine production, but may also be applied to discriminating eggs just prior to or in the process of harvesting vaccine in a vaccine production process. Embodiments of this invention may also be used for collecting data that is used to predict the numbers of eggs that will hatch in situations where milky eggs are present even in smaller quantities such as Day 9 to 14 eggs in a broiler hatchery.

Experimental Data

Figure 6:
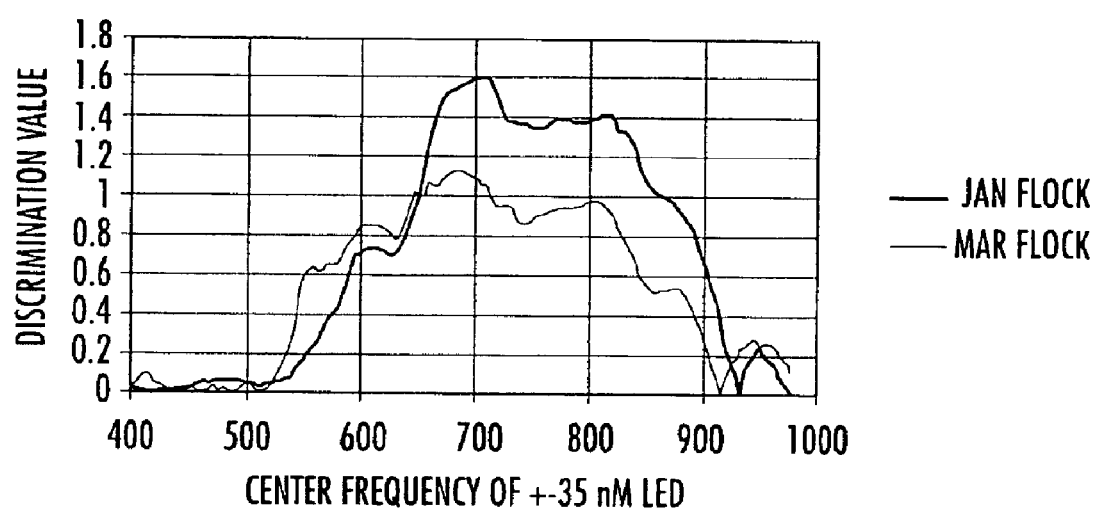
FIG. 6 is a graph showing the ability of a single beam to discriminate between live and non-live day 11 eggs.

In order to discover the combinations of LED light sources that would best discriminate among live Day-11 and milky eggs, extensive spectrophotometer data for these types of eggs was collected and analyzed to establish optimal regions. FIG. 6 is a plot of the potential for discriminating between live and milky eggs using LED generated light of different wavelengths. Note that wavelengths between 600 and 850 nM are much more effective than visible or 880 nM light, and the range from 650 to 820 is most effective. This plot was created in the following manner:

1. Two groups of approximately 1300 Day-11 eggs were run tested by a standard Embrex 880 nM Identifier. The 5% of the eggs that had light values closest to the live-dead cutoff value were selected, hand candled and broken out to establish embryo condition. In the difficult to screen group were 51 live and 30 milky eggs from a January flock and 43 live and 24 milkies from a March flock.

2. Spectrometry data was collected for these two groups of eggs by shining a narrow beam of light from a tungsten halogen light downwards at the top (aircell end) of each egg. A fiber optic cable and collimating lens aimed at the bottom of each egg carried light to an Ocean Optics spectrometer. The spectrometer gave the light intensity for two thousand light wavelengths evenly spaced between 400 nM and 1000 nM. Each value was effectively the transmissibility of each egg at that wavelength.

3. The two thousand points of spectral data for each egg were used to synthesis an effective transmissivity of light that would occur at a wide bandwidth detector when from light from an LED having a half-power spectral band of ±35 nanometers was shined at the top of each egg. This was done for each of about 110 imaginary LEDs with center wavelengths at 5 nM intervals from 420 to 980 nM.

4. Using the light values projected to be transmitted through eggs for each imaginary LED, the mean and standard deviation statistics were calculated for the live and milky eggs from each flock. A quantitative measure of the accuracy of discrimination between lives and milkies was defined as the arithmetic difference between the live and milky means divided by the square root of the sum of the square of the live standard deviation and the square of the milky standard deviation. A large discrimination value thereby indicates that the two groups of eggs have very different light values at that wavelength relative to the variation within each group.

5. This data is plotted in FIG. 6 for the two groups of live and milky eggs. Note that these eggs were preselected to be the live and milky eggs out of 1300 eggs that are most difficult to discriminate with 880 nM LED technology, so that the discrimination ratios predict which wavelengths work best for the eggs that are most difficult to discriminate. The discrimination values are not true discrimination values for the entire population of eggs.

Figure 7:
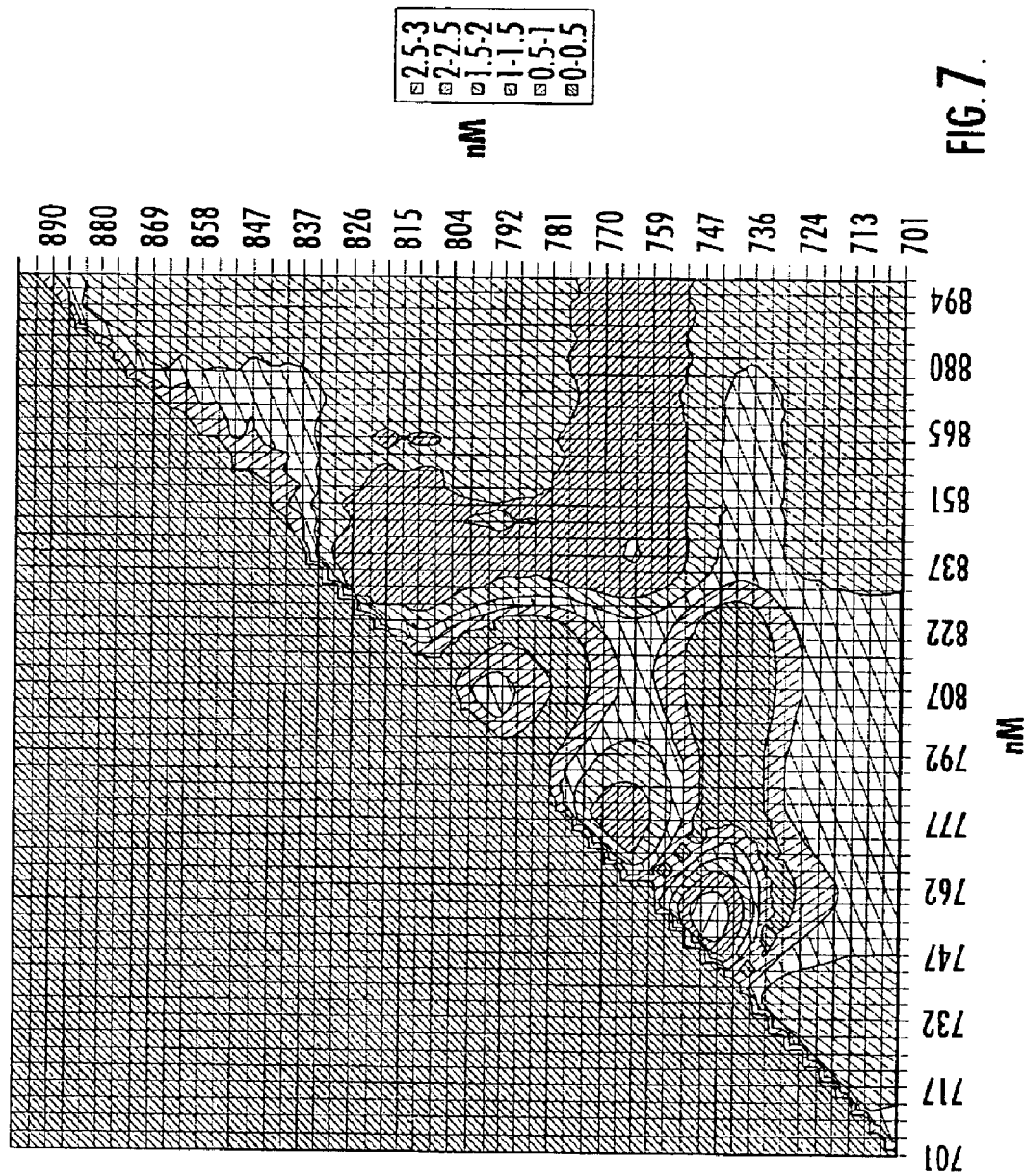
FIG. 7 is a plot showing the combinations of wavelengths that allow discrimination between live and non-live day 11 eggs.

The same data set was used to discover the combinations of LED light sources that would discriminate lives from milkies based upon a ratio of received light intensities. This data is plotted in FIG. 7. In this case analysis was done to discover that the ratios of intensities at the two wavelengths gave the highest discrimination values. In FIG. 7, there are zones of discrimination values. Here, orange is a high value, and light blue is lowest. Discrimination values better than 1.5 give good machine performance.

Figure 8:
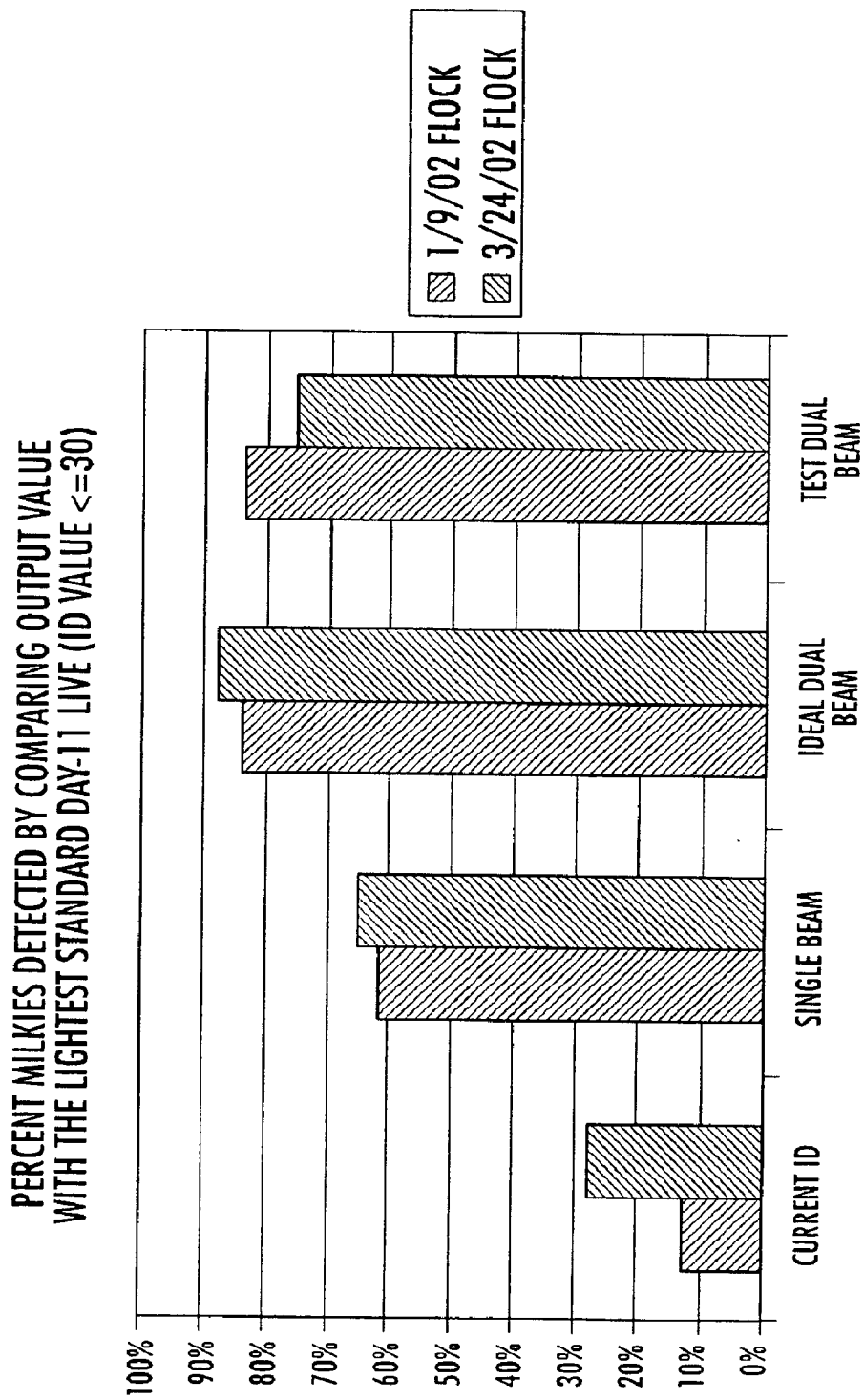
FIGS. 8–9 are graphs comparing the performance of various LED light sources, according to embodiments of the present invention.

FIG. 8 is a graph that compares the performance of a standard 880 nM Identifier, a 700 nM single-beam Identifier, a dual Beam Identifier using 760 and 880 nM (Ideal) and 750 and 880 nM "test" dual beam unit. The eggs used were the select group of the 5% most difficult to classify eggs as determined by the standard 880 nM Identifier. The percentage of the eggs classified correctly using as a cutoff the one live egg whose value is nearest the milky eggs. Note that one live egg believed to be a runt with a light level more than three times the mean live egg value on the 880 Identifier was excluded from this comparison.

Figure 9:
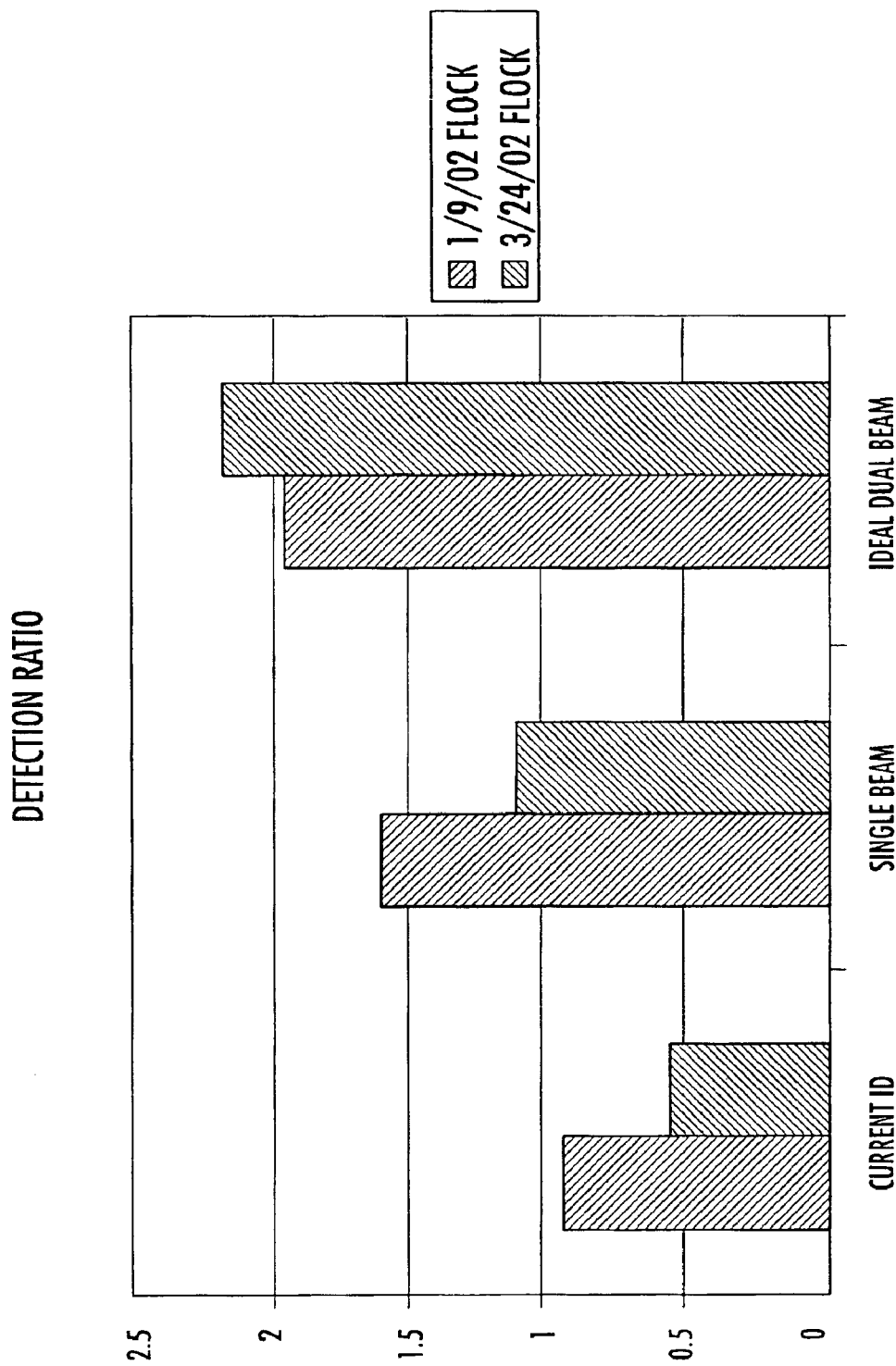

FIG. 9 is a graph that compares the performance of the standard 880 nM Identifier, a 700 nM single-beam Identifier and a dual Beam Identifier using 760 and 880 nM (Ideal). The eggs used were the select group of the 5% most difficult to classify eggs as determined by the standard 880 nM Identifier. Detection ratio was calculated as the difference between the means of the lives and dead eggs divided by the square root of the sum of the squares of the standard deviations of the two groups.

Figure 10:
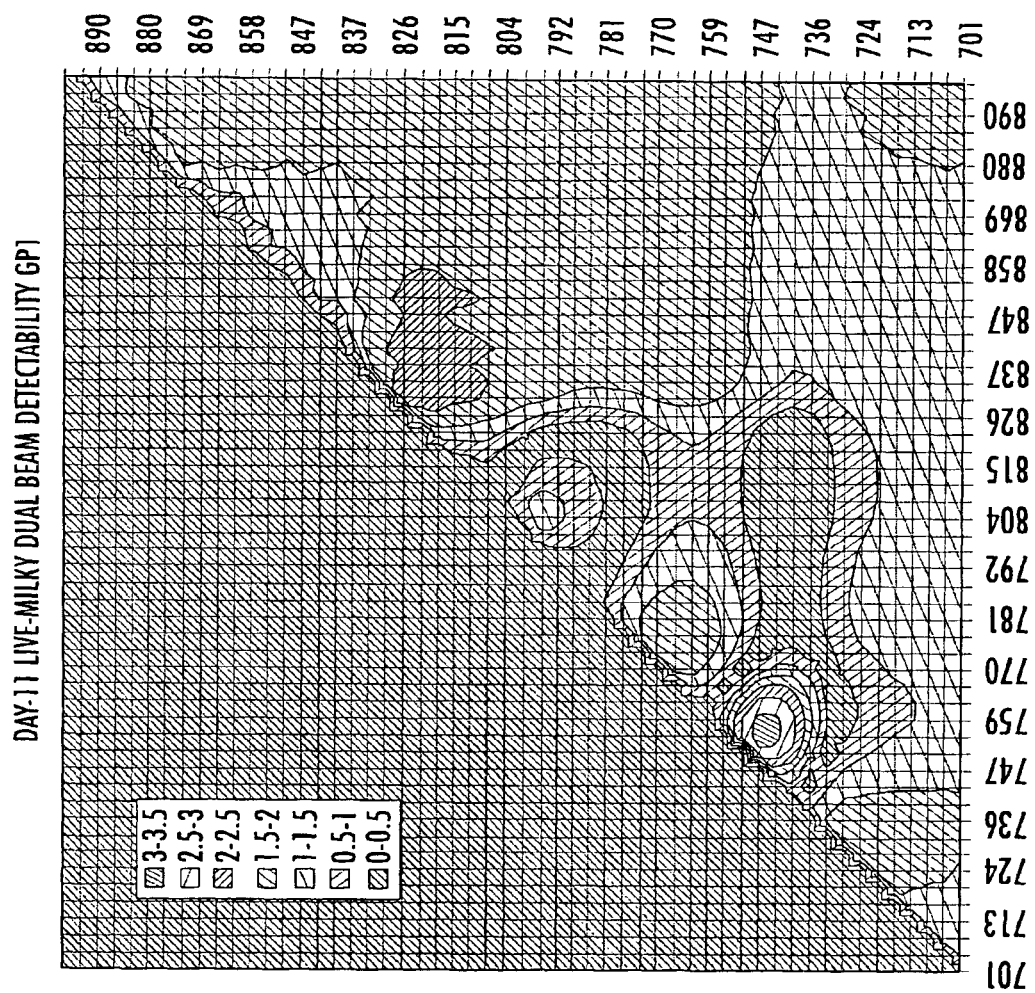

FIGS. 10–11 are respective plots showing the discrimination ratio for the two groups of selected eggs using a number equal to the ratio of light values at two different wavelengths. High values indicate the mean values for the lives and milkies are well separated relative to their variation. The two groups of eggs are the 5% most difficult to separate eggs in the January (Group 1) and March (Group 2) flocks.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

That which is claimed is:

1. A method of identifying whether an egg contains a live embryo, comprising:
    illuminating the egg with one or more pulses of light from a light source at wavelengths of between about 650 nm–850 nm for a time period of less than or equal to about 1 second, wherein the one or more pulses of light have a peak wavelength of between 650 nm and 820 nm and a half-power spectral width of less than about 100 nm;
    receiving light passing through the egg at a detector positioned adjacent the egg; and
    identifying the egg as containing a live embryo if detected light is less than a preset value, or identifying the egg as a non-live egg if detected light is greater than the preset value.

2. The method of claim 1, wherein the light source and detector are positioned on respective opposite portions of the egg.

3. The method of claim 2, wherein the light source and detector are positioned on respective opposite end portions of the egg.

4. The method of claim 1, wherein the light source comprises a light emitting diode (LED).

5. The method of claim 1, wherein the egg is in day eleven of incubation (day-11 egg).

6. A method of producing a vaccine within a plurality of eggs, comprising:
    illuminating each egg with one or more pulses of light from a light source having a peak wavelength of between 650 nm and 820 nm and a half-power spectral width of less than about 100 nm for a time period of less than or equal to about 1 second;
    receiving light passing through each egg by a detector positioned adjacent each egg;
    identifying a egg as containing a live embryo if detected light for the egg is less than a preset value, or identifying the egg as a non-live egg if detected light for the egg is greater than the preset value; and
    injecting a virus into each egg identified as containing a live embryo.

7. The method of claim 6, further comprising discarding each egg identified as a non-live egg.

8. The method of claim 6, wherein the light source and detector are positioned on respective opposite portions of each egg.

9. The method of claim 8, wherein the light source and detector are positioned on respective opposite end portions of each egg.

10. The method of claim 6, wherein the light source comprises a light emitting diode (LED).

11. The method of claim 6, further comprising:
    euthanizing an embryo in each egg identified as containing a live embryo; and
    harvesting amniotic fluid from each euthanized egg, wherein the amniotic fluid comprises vaccine.

12. The method of claim 11, wherein the virus comprises human flu virus and wherein the harvested amniotic fluid comprises human flu vaccine.

13. The method of claim 6, wherein the egg is in day eleven of incubation (day-11 egg).

* * * * *